United States Patent [19]
Beffy et al.

[11] Patent Number: 5,513,532
[45] Date of Patent: May 7, 1996

[54] METHOD AND APPARATUS FOR DETECTING INTERNAL DEFECTS

[75] Inventors: Lionel Beffy, Juvisy; Najet Chakroun, Villeneuve La Garenne; Alexandre M. Fink, Meudon; Gérard Y. Mangenet, Epinay Sous Senart; François J. Wu, Orsay, all of France

[73] Assignee: Societe Nationale d'Etude et de Construction de Moteurs d'Aviation (S.N.E.C.MA.), Paris, France

[21] Appl. No.: 153,190

[22] Filed: Nov. 17, 1993

[30] Foreign Application Priority Data

Nov. 18, 1992 [FR] France ................... 92 13834

[51] Int. Cl.⁶ .................................. G01N 29/04
[52] U.S. Cl. .................................. 73/628; 73/641
[58] Field of Search ................ 73/602, 606, 625, 73/626, 628, 641

[56] References Cited

U.S. PATENT DOCUMENTS

| | | |
|---|---|---|
| 3,961,523 | 6/1976 | Cornforth . |
| 4,375,165 | 3/1983 | de Sterke ............ 73/637 |
| 4,463,608 | 8/1984 | Takeuchi et al. .......... 73/606 |
| 4,665,734 | 5/1987 | Joet .................... 73/640 |
| 4,872,130 | 10/1989 | Pagano ................. 73/637 |
| 5,092,236 | 3/1992 | Fink . |

FOREIGN PATENT DOCUMENTS

| | | |
|---|---|---|
| 0081244 | 6/1983 | European Pat. Off. . |
| 0486689 | 5/1992 | European Pat. Off. . |

Primary Examiner—Richard Chilcot
Assistant Examiner—Max H. Noori
Attorney, Agent, or Firm—Bacon & Thomas

[57] ABSTRACT

A method and apparatus for detecting internal defects in a workpiece are disclosed which uses time inversion to invert echo signals received by a transducer from the workpiece with respect to the signal shape and its time distribution and retransmits the inverted signal onto the workpiece. The method involves transmitting an unfocused ultrasonic beam onto the workpiece, receiving an echo signal from the workpiece, storing the first echo signal and inverting the first echo signal from each transducer with respect to the signal shape and time sequence. The inverted signal is transferred to a memory and the aforementioned procedure is carried out for each of the inspection zones n on the workpiece. The stored, inverted first echo signals are then transmitted onto the workpiece, each inverted signal being transmitted onto the inspection zone n from which the non-inverted first echo signal was received. A second echo signal is received for each inspection zone n of the workpiece and this second echo signal is also inverted with respect to both the signal shape and the time sequence and again stored in a memory. The second, inverted echo signal may be again be retransmitted onto the workpiece in the same inspection zone n from which the first, inverted echo signal was transmitted. The apparatus used for carrying out this method may comprise an array of ultrasonic transducers located adjacent to the workpiece so as to direct ultrasonic energy onto an inspection zone n of the workpiece, a first memory connected to transducer array to receive first echo signals from the transducer and to invert the echo signals with respect to both the signal shape and the time sequence. A second memory is used to store the inverted first echo signals from the first memory and is connected to the transducer array such that these first inverted echo signals may be retransmitted onto the workpiece in the inspection zone from which the corresponding non-inverted echo signal was received.

14 Claims, 6 Drawing Sheets

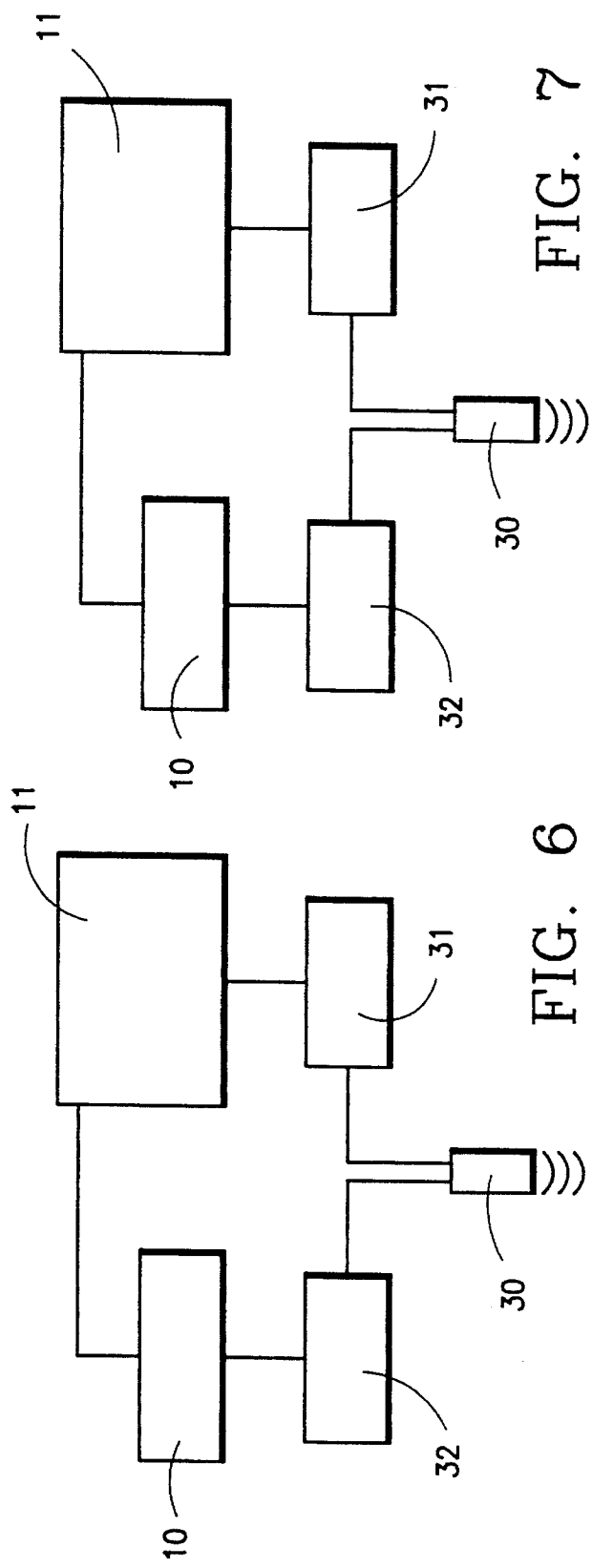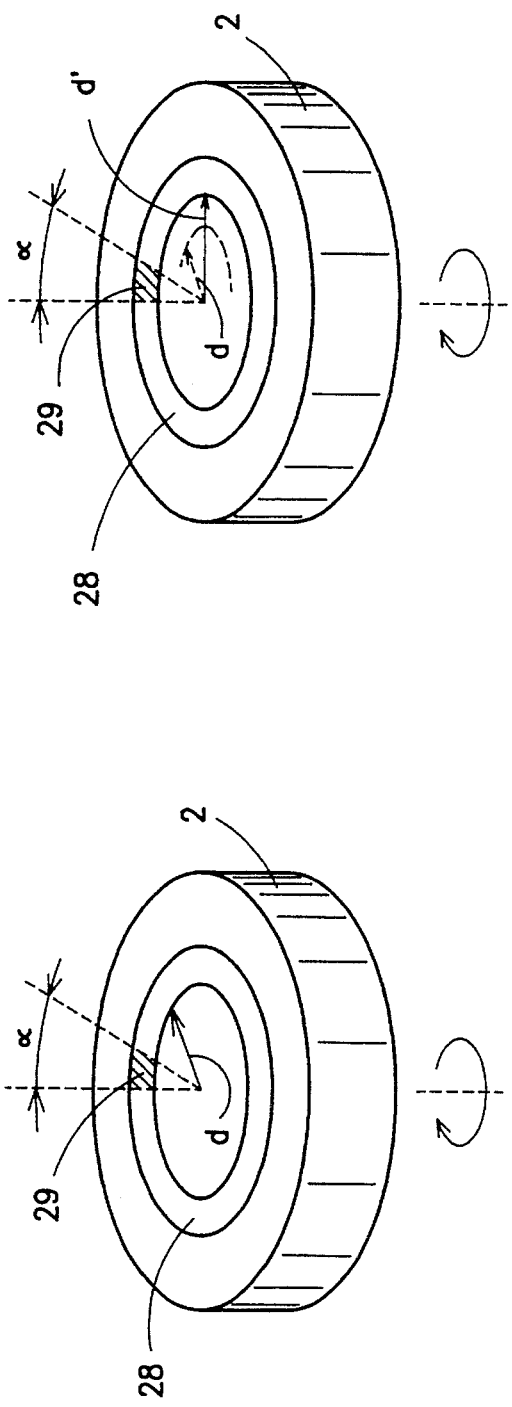

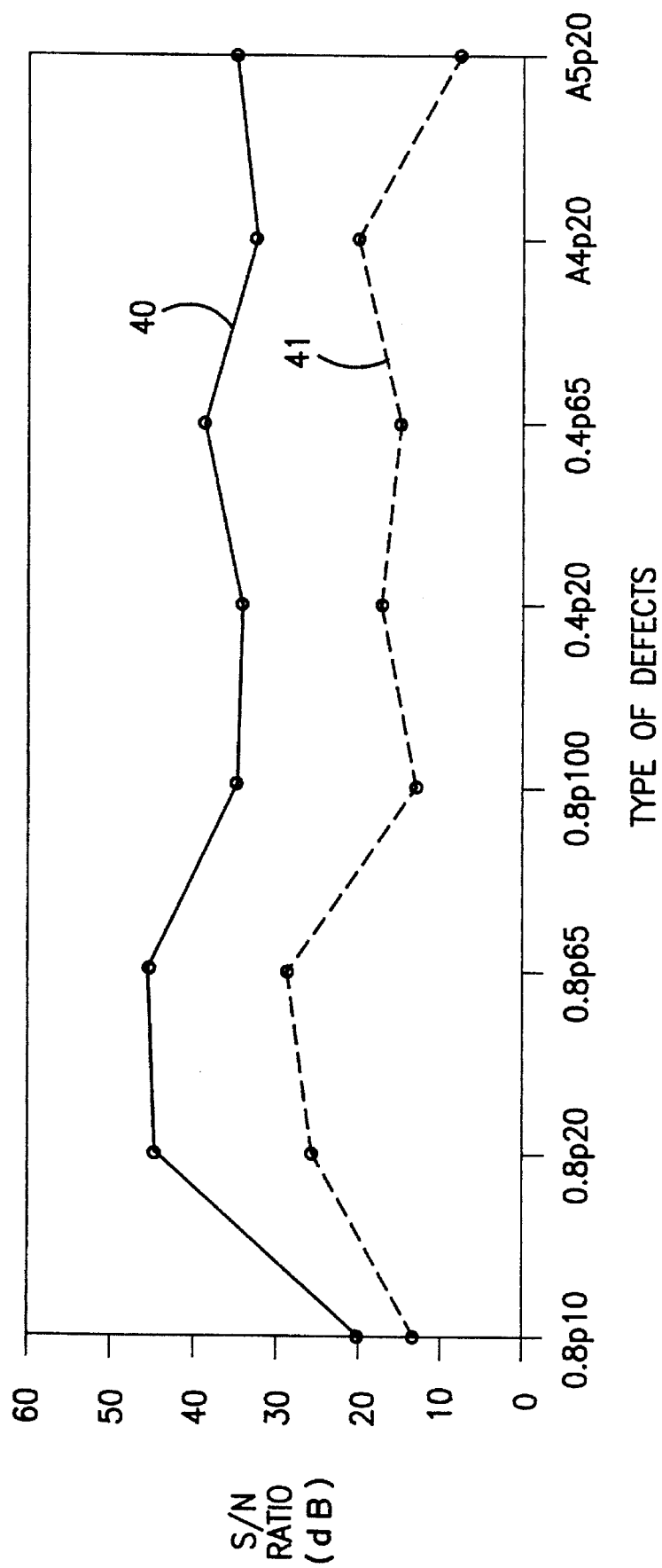

METHOD AND APPARATUS FOR DETECTING INTERNAL DEFECTS

BACKGROUND OF THE INVENTION

The present invention relates to a method and an apparatus for detecting internal cracks, fractures, or other defects in a workpiece utilizing ultrasonic techniques with time inversion.

Ultrasonic, non-destructive testing systems are known and such are especially well-suited for testing metal workpieces to detect any internal defects. However, such known systems lack accuracy when attempting to locate a heterogeneity in complex materials, such as special alloys, composites, ceramics, or materials made by powder metallurgy. It is difficult, or even impossible, to use echo signals generated by an ultrasonic transducer in the aforementioned materials and, more particularly, in titanium, due to the presence of substantial noise echoes arising from the diffusing nature of such materials.

U.S. Pat. No. 5,092,336 discloses an apparatus for locating and focusing ultrasonic waves primarily intended for research purposes, and for the destruction of calculi in human tissue. This apparatus makes use of a phase-conjugate ultrasonic amplification procedure, also known as "time inversion". Following generation of an unfocused ultrasonic beam onto the material and receiving an echo returned to a transducer, this system inverts both the time distribution and the shape of the returned echo and retransmits this inverted signal into the material. However, this essentially static procedure cannot be used under industrial situations, particularly to detect defects in workpieces, particularly those of revolution about an axis of symmetry, since it requires complex, high-performance systems allowing short order alternation of the motions and stops required for the auto focusing feature of this procedure.

SUMMARY OF THE INVENTION

A method and apparatus for detecting internal defects in a workpiece are disclosed which uses time inversion to invert echo signals received by a transducer from the workpiece with respect to the signal shape and its time distribution and retransmits the inverted signal onto the workpiece. The method involves transmitting an unfocused ultrasonic beam onto the workpiece, receiving an echo signal from the workpiece, storing the first echo signal and inverting the first echo signal from each transducer with respect to the signal shape and time sequence. The inverted signal is transferred to a memory and the aforementioned procedure is carried out for each of the inspection zones n on the workpiece. The stored, inverted first echo signals are then transmitted onto the workpiece, each inverted signal being transmitted onto the inspection zone n from which the non-inverted first echo signal was received. A second echo signal is received for each inspection zone n of the workpiece and this second echo signal is also inverted with respect to both the signal shape and the time sequence and again stored in a memory. The second, inverted echo signal may be again be retransmitted onto the workpiece in the same inspection zone n from which the first, inverted echo signal was transmitted.

The apparatus used for carrying out this method may comprise an array of ultrasonic transducers located adjacent to the workpiece so as to direct ultrasonic energy onto an inspection zone n of the workpiece, a first memory connected to the transducer array to receive first echo signals from the transducer and to invert the echo signals with respect to both the signal shape and the time sequence. A second memory is used to store the inverted first echo signals from the first memory and is connected to the transducer array such that these first inverted echo signals may be retransmitted onto the workpiece in the inspection zone from which the corresponding non-inverted echo signal was received.

The use of a "time inversion" procedure makes possible the improved focusing of the ultrasonics onto the internal defect of the analyzed workpiece, thereby eliminating most of the spurious noise echoes. The elimination of the noise echoes ensures that the aforementioned material may be inspected for internal defects more reliably than with the known systems.

The "time inversion" of the echo signals received from the workpiece followed by the subsequent transmission of these inverted signals onto the workpiece may be repeated until the precise location and shape of the internal defect is known. Thereupon, a decision can be made as to whether or not to reject the workpiece. The apparatus also involves devices for moving the workpiece relative to the transducer array such that the entire workpiece may be inspected.

The second memory of the apparatus may be a circulating buffer wherein the data to be transmitted from the transducer array, the time inverted signals, relate to a specific inspection zone and are stored in the memory such that the inverted signals are reapplied to the same inspection zone from which the previous echo signals were obtained. This can be achieved by synchronizing the rotation of the workpiece with the transmitter control of the transducer array to allow consecutive retransmissions at the same work inspection zones to reinforce the auto-focusing upon each rotation of the workpiece. The transmission synchronization may be implemented by using a comparator which compares the coordinates of the transmitting points of each inspection zone previously stored in a memory register with the actual component coordinates measured by an encoder.

BRIEF DESCRIPTION OF THE DRAWINGS

FIGS. 6 and 7 are schematic diagrams illustrating an alternative mode of the method according to the present invention.

FIG. 9 is a graph comparing the signal-to-noise ratio of the time inversion method according to the present invention with the signal-to-noise ratio of prior art systems.

DETAILED DESCRIPTION OF THE PREFERRED EMBODIMENTS

Figure 1:
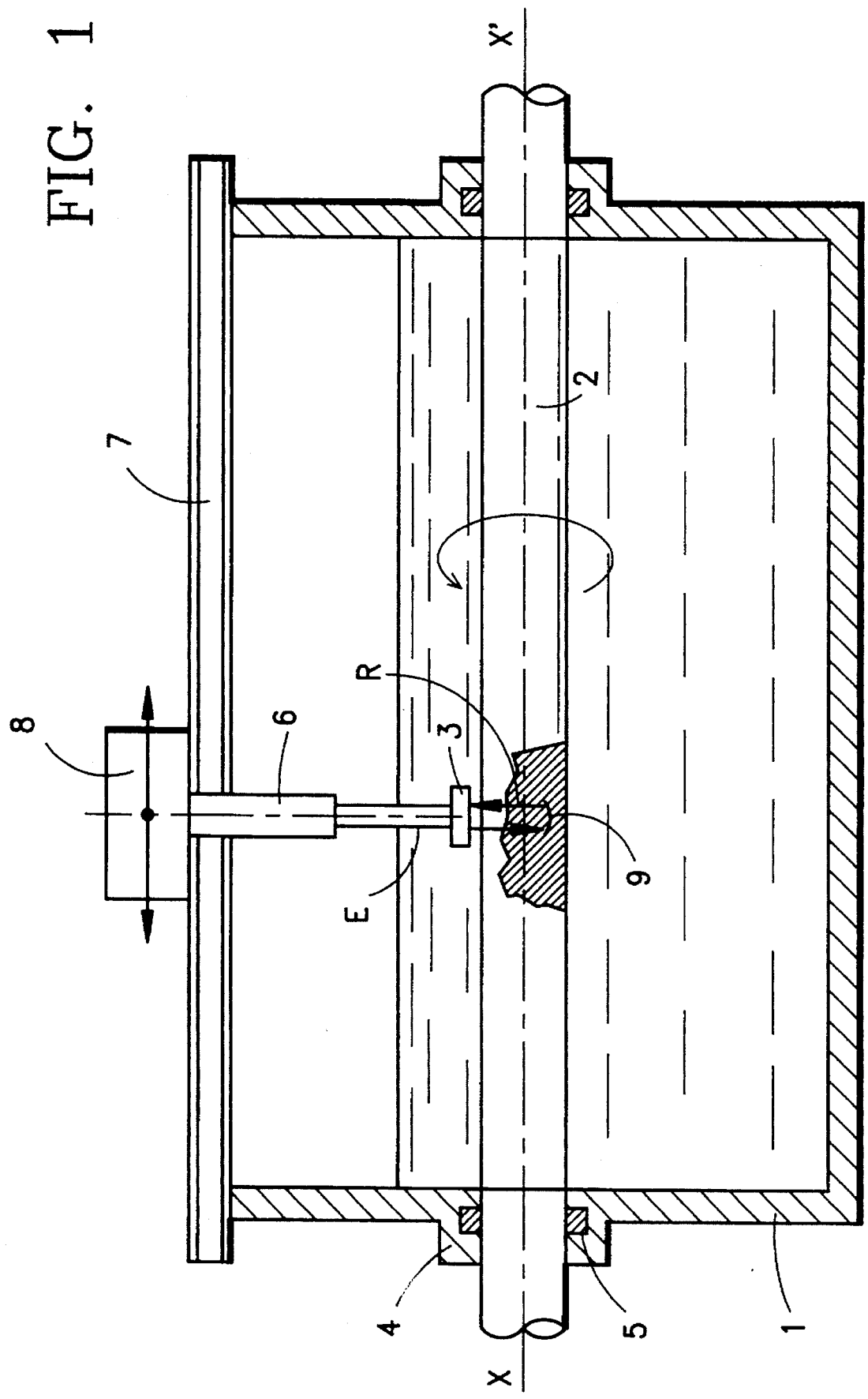
FIG. 1 is a diagrammatic, longitudinal, sectional view of the ultrasonic test equipment according to the present invention.

FIG. 1 is a longitudinal, sectional view of an ultrasonic testing equipment for testing a workpiece 2 having an axis of revolution X-X', which may be a titanium rod. The testing equipment comprises a tub 1 filled with an acoustic coupling liquid of which the surface level is kept constant by a known leveling system (not shown). For the sake of clarity, the liquid supply and drain conduits have not been illustrated in FIG. 1.

A workpiece 2 to be tested and an ultrasonic detector 3 are immersed in the acoustic coupling liquid in the tub 1. Bearings 4 assure that the workpiece 2 is centered along its axis X-X', while seals 5 prevent leakage of the coupling liquid from the tub 1. The detector 3 is kept strictly perpendicular to the axis X-X' by a support 6 which is adjustable to vary the distance between the detector 3 and the workpiece 2. The apparatus also includes means (not shown) to rotate workpiece 2 about its axis X-X' and a drive means 7 and 8 by which the detector 3 may be displaced with respect to the workpiece in a direction generally parallel to the axis X-X'. The detector 3 is a transceiver comprising a plurality of piezo-electric elements arranged in an array in a matter to be described in more detail below.

The use of the immersion tub 1 is advantageous insofar as it avoids direct contact between the detector 3 and the workpiece 2, the acoustic coupling being assured by the coupling liquid, which may comprise water having wetting agents such as oil. However, total immersion is not mandatory within the scope of the instant invention and the testing may be carried out by merely placing the detector 3 against the workpiece 2 using only a thin coupling film between them.

The testing principle rests on generating an ultrasonic wavetrain E which penetrates the workpiece 2 and detecting the reflected portion R which is reflected by an internal defect 9 within the workpiece 2. The rate at which the consecutive wave trains are generated is called the test repeat frequency. The workpiece 2 rotates while being tested and the testing may be carried out continuously.

Within the scope of the invention, testing takes place by either a step-wise, longitudinal displacement of the detector 3, or, when analyzing relatively thin disk-like workpieces, the testing may take place by sequentially analyzing annular portions of the disc until the entire workpiece has been tested.

Figures 2, 3:
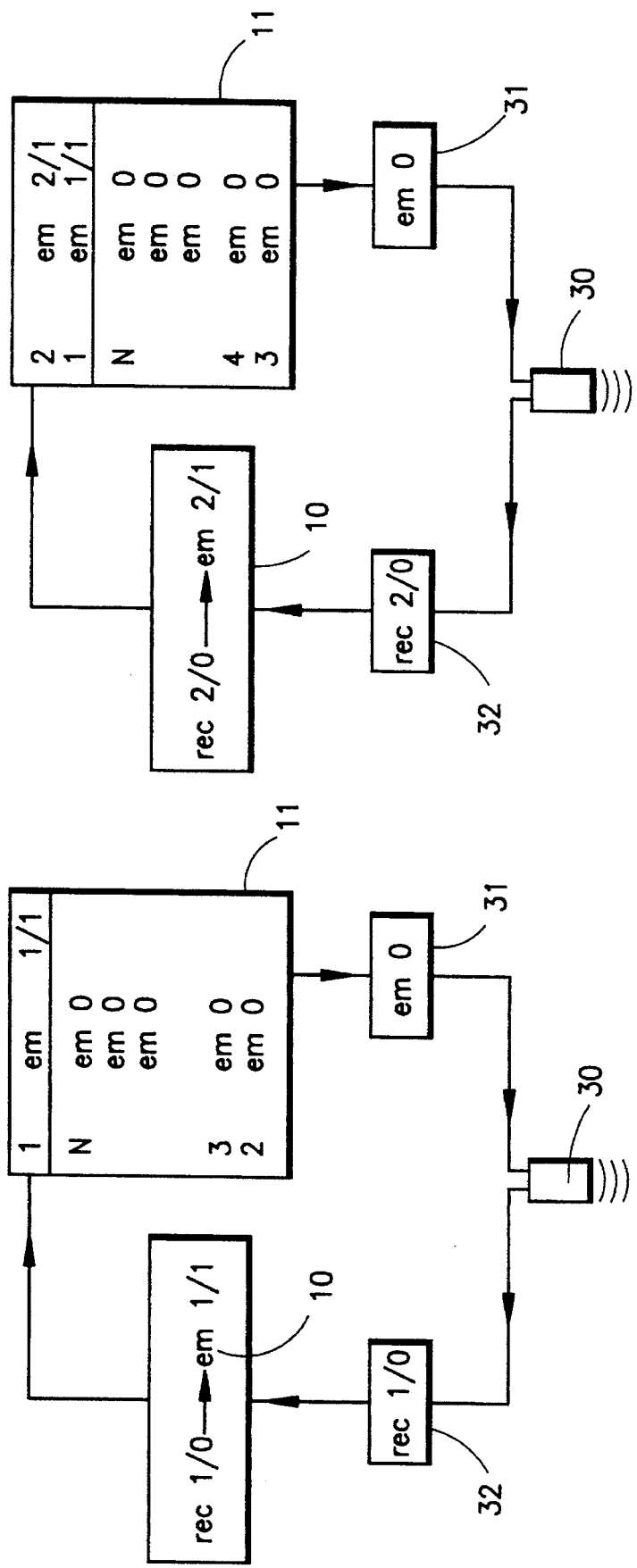
FIGS. 2–5 are schematic diagrams illustrating the implementation of the method according to the present invention.

FIGS. 2–5 schematically illustrate the steps of the invention regarding the testing of a workpiece. As illustrated in FIG. 2, the array of transducers 30 generate an unfocused ultrasonic beam which illuminates the circumferential area of inspection sector 21 of the workpiece 2. The sector 21 is accurately defined such that the workpiece is divided into n-number of inspection zones angularly equidistant about the circumference of the workpiece 2.

The echo received by each of the transducers in the array is picked up and the time distribution as well as the shape of each echo signal received from each transducer is stored in a first memory 10. According to the time inversion principal described in U.S. Pat. No. 5,092,336, these echo signals are then time inverted with respect to both their shape and their sequence in time. By inverting the time sequence, the last received signals are returned first and vice versa. The inverted signals are then stored in a second memory 11. The procedure of transmitting an unfocused ultrasonic beam, storing the echo received, time inverting the echo signal and storing it in the second memory are then carried out for each of the inspection sectors n. Upon completion of the testing of the sectors extending around the entire circumference of the workpiece 2, the first time inverted signal will be available at the output of the second memory 11 to be transmitted onto the workpiece 2 in the sector 21 from which the first non-inverted echo signal was received. The transmission of the time inverted signal for each particular inspection sector is carried out until the entire circumference of the workpiece 2 has been covered.

The transmission by the transducer array allows the generation of an accurately focused wave to the extent that the transducer response is linear, or that it possesses the same properties for transmitting and receiving. Furthermore, the distortions encountered on the way to and caused by diffusion in the workpiece 2 are precisely compensated by the distortions on the way back. Subsequent to the second transmission of the time inverted signal, each transducer receives an echo to generate a second echo signal which, again, is stored in first memory 10 and once again time inverted and stored into the second memory 11.

These two transceiving phases are then repeated for each of the other inspection sectors in order to cover the entire portion of the workpiece. Each time the transmitted signals are those resulting from the previous time inversion of the echo signals from the unfocused ultrasonic beam transmitted to the particular inspection sector zone.

Upon completion of the testing of this particular portion of the workpiece, the second inverted echo or actuation signals, relating to each of the n sectors are stored in the second memory 11. This transceiving procedure can be carried out as often as desired with the actuation signals resulting from each new generation being stored in the second memory 11 in place of the actuation signals of the previous generation. In practical terms, two focused generations following the initial unfocused generation (three passes) will suffice to ascertain the largest defect. However, this number is not limiting and, in extreme cases, it may be possible to ascertain this defect after the first pass.

The focused and unfocused ultrasonic beams are supplied from an array of transducers 30 which may be a linear or a two dimensional array. In known fashion, the array may be planar, or may be possibly concave to ensure the beam will be geometrically prefocused with respect to the workpiece. Each transducer is associated with a processing channel comprising a receiver 32 which receives the signal generated by the echo and transmits this signal to a first memory 10 whose output is the time inverted echo signal. The configuration of the receiver-memory assembly may be identical with that in the above-cited patent and it may illustratively comprise a sampler, an analog-digital converter and a LIFO (last in first out) type memory. The initial beam is generated by a transmitter 31 which receives signal transmission data from second memory 11 which, in turn, receives the time inverted echo signals from the first memory 10.

FIG. 2 illustrates the data stored in the second memory 11 after a first transceiving of an unfocused ultrasonic beam onto the first inspection zone 21. The first memory location is denoted by I corresponding to the first tested inspection zone 21 that initially comprised the time distribution and the shape of the unfocused signal em 0 now is loaded by the actuation signal em1/1 corresponding to the received echo signal 1/0 in response to the transmission of the unfocused signal em 0. The memory location is a set of memory-element locations each able to receive a sample of the received signal, the number of samples depending upon the sampling rate of the signal and the time of observation taking into account the echoes. Moreover, the unfocused wavetrain corresponding to the simultaneous generation for all these transducers of a short pulse, the signal em 0 advantageously shall be constituted of a set of null values, except for a number related to the sampling rate.

FIG. 3 illustrates the data stored in the second memory 11 upon the testing of a second inspection sector 22 which is displaced from the first inspection sector 21 via angle α. This figure illustrates that the second memory location denoted 2 and initially loaded by the signal em 0 (see FIG. 1), presently stores the actuation signal 2/1 corresponding to the inverted echo signal issuing from the received echo signal 2/0 in response to the signal em 0 at the second sector 22. Once the n inspection sectors have been tested, the second memory 11 will be loaded with N actuation signals em1/1-emN/1 occupying n memory locations.

Figures 4, 5:
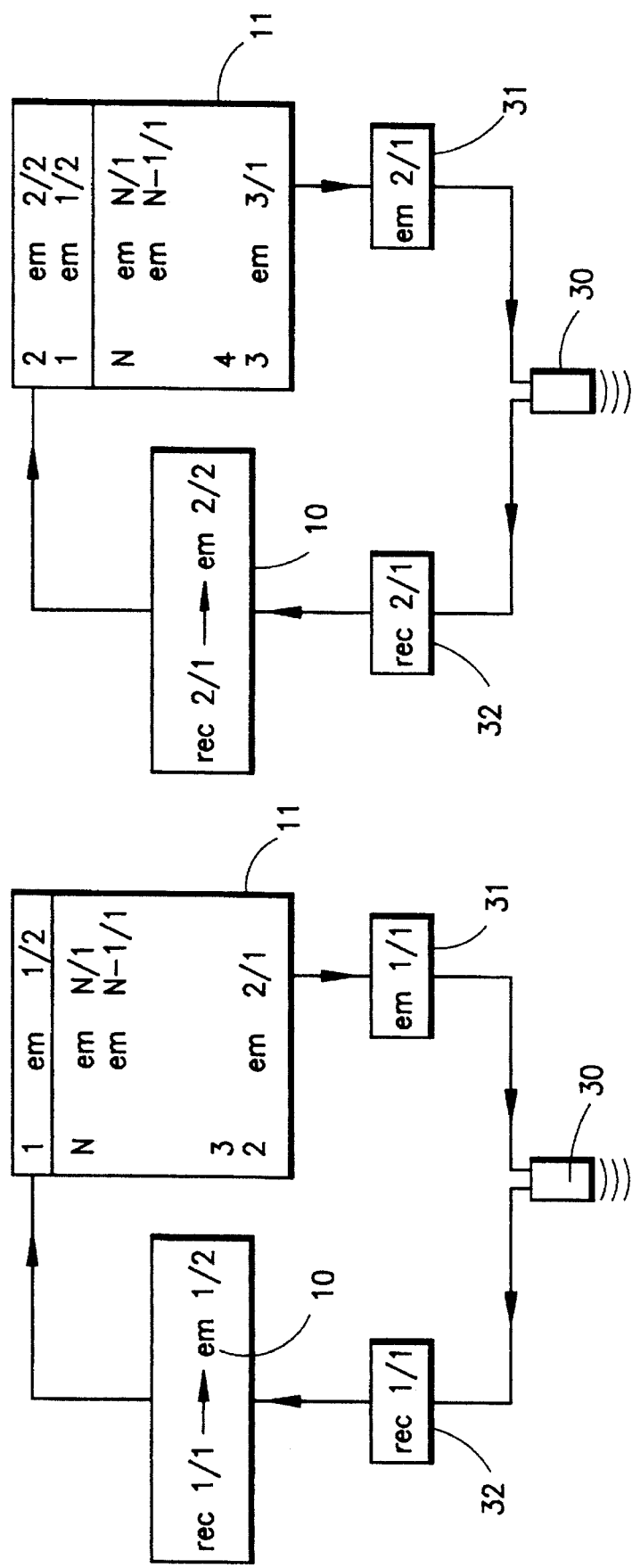

FIG. 4 illustrates the data stored in the second memory 11 upon the second testing pass of the first inspection sector 21. To ensure proper equipment functioning, the consecutive transmissions toward the same inspection sector must be in the same places, which is accomplished by a synchronization system which will be described in more detail below. In its first location, the memory 11 holds the actuation signal em1/2 corresponding to the time inverted echo signal from the received echo signal rec 1/1 in response to the transmission of the previously stored actuation signal em1/1 onto the first inspection sector 21. Obviously, in the other inspection locations, there will be other actuation signals em 2/1 through em N/1 corresponding to the other inspection sectors. Testing the next sector 22 (FIG. 5) entails loading a second actuation signal em 2/2 into the second memory 11 replacing the previous signal em 2/1 obtained from the test of the previous pass. At the end of testing, upon completion of this second pass, the second memory 11 will be loaded with N actuation signals em 2/2 through em N/2.

The above procedure may be repeated as often as necessary to ascertain the internal defects in the workpiece to be tested in an auto-focus manner. Following i number of passes, the second memory will be loaded with actuation signals em 1/i through em N/i.

FIGS. 6 and 7 illustrate a second embodiment of the invention which is utilized to test workpieces having a relatively thin, disc-like configuration. Again, the testing is continuous and may be carried out while workpiece 2 is rotating. In this embodiment, the testing is carried out on consecutive annuli 28 with the transducer array 30 being displaced relative to the workpiece 2 generally perpendicular to the rotational axis of the workpiece, in this particular instance, a radial direction by a step d-d' which will allow full workpiece testing. The testing is carried out on n number of inspection sector elements 29 of the annulus 28 in a manner similar to that described in regard to the previous embodiment.

Figure 8:
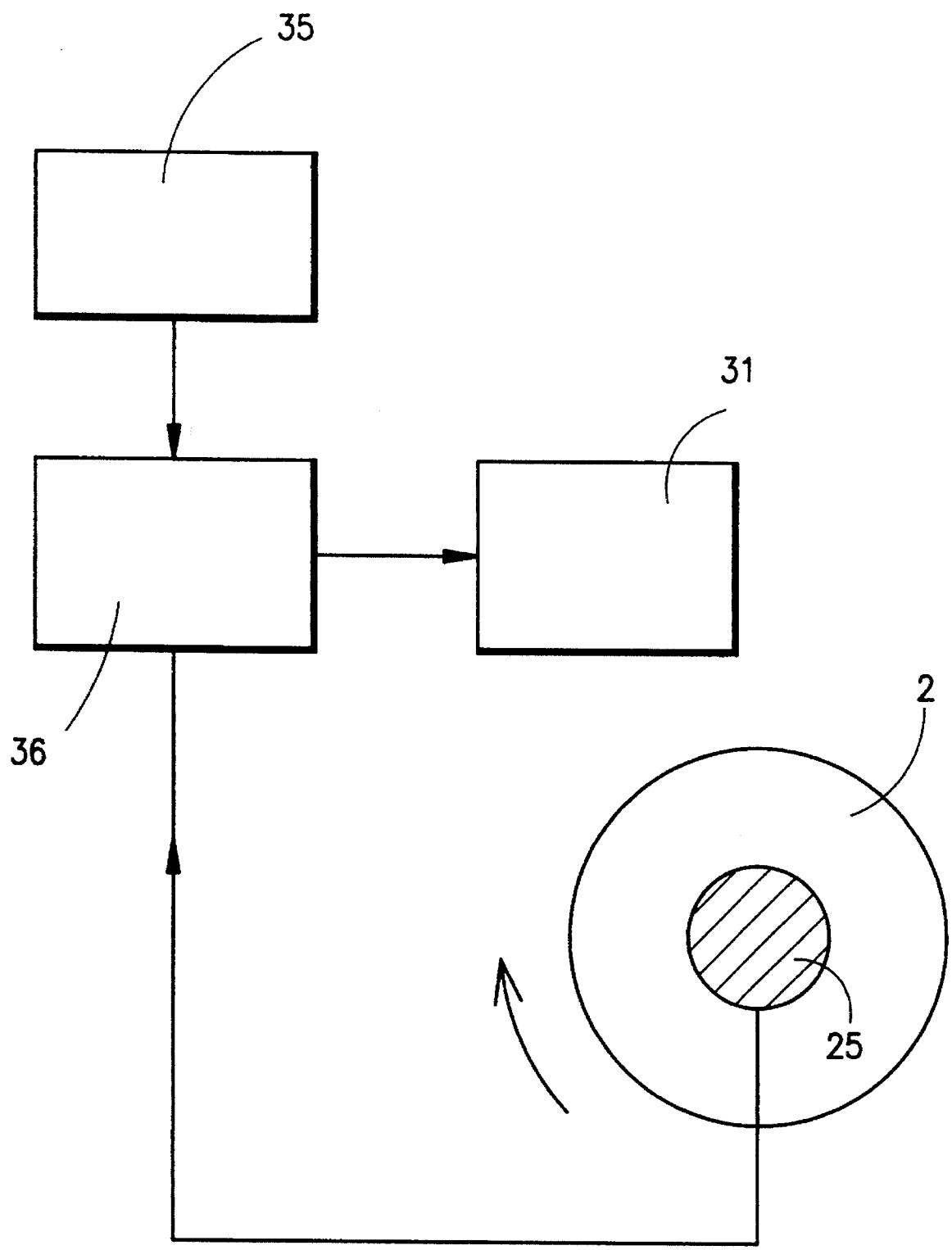
FIG. 8 is a schematic diagram illustrating the synchronization apparatus according to the present invention.

FIG. 8 is a schematic diagram of the means for synchronizing the transmissions of the various signals to either the circumferential area of a given inspection sector, or the area of a given inspection sector element. An encoder 25 is associated, in known fashion, with the means rotating the workpiece 2 such that it accurately determines the angular position of the workpiece relative to a given reference. Preferably, the encoder will be an absolute digital encoder. The coordinates of the positions of the various signal transmissions are input into a memory register 35 which is connected to comparator 36, as is encoder 25. Comparator 36 compares the stored coordinates with the actual coordinates sensed by the encoder 25 and controls the transmitter 31 of the transducers. As the workpiece 2 rotates, the various transmissions are consecutive in step with the coincidence between the angular coordinates of the workpiece 2 supplied by the encoder 25 with those stored in the memory register 35. Obviously, no limitation is implied by the use of an absolute encoder, since such synchronization can also be achieved by using an incremental encoder.

FIG. 9 is a graph comparing the performance of the instant time inversion method and a conventional testing method for non-destructive ultrasonic testing, specifically comparing the signal-to-noise ratio, The actual tangential speeds when testing are approximately 500 mm/s and result in a transceiving repeat rate of 50 Hz for an advance pitch of 10 mm, which are quite compatible with industrial goals, in particular regarding the testing time. For the known testing technique, measurements were taken using a conventional focused transducer in a conventional ultrasonic testing procedure, while composite-ceramic transducers were utilized for measurements regarding the time inversion method according to the present invention. The tested component was a titanium disc 100 mm in diameter into which two kinds of defects were machined: machined flat bottom holes 0.4 and 0.8 mm in diameter with variable depths of 10, 20, 65 and 100 mm, as well as inclusions of powder-metallurgy impurities with diameters of 1.1 mm (A4) and 0.7 mm (A5) and 20 mm deep. Testing was carried out with a 120 mm constant-height water column at a frequency of 3 MHz. These testing conditions should not be construed as in any way limiting this invention, since other tests have been carried out under different conditions, for instance at 5 MHz.

All of the above defects were detected and, as can be seen in FIG. 9, the present time-inversion method represented by curve 40 performs far better than the conventional method, illustrated by curve 41 since the former offers a signal-to-noise ratio of at least 20 dB with portions as high as almost 30 dB. It is evident that the testing for internal defects by the method according to the present invention is superior to the known techniques, and further improvements may be obtained by optimizing the transducer array with respect to the transducer size and their radii of curvature, among other factors.

The foregoing description is provided for illustrative purposes only and should not be construed as in any way limiting this invention, the scope of which is defined solely by the appended claims.

We claim:

1. A method for detecting internal defects in a workpiece comprising the steps of:

a) providing an array of ultrasonic transducers;

b) positioning the workpiece so as to position a first inspection zone adjacent to the array of ultrasonic transducers;

c) transmitting an unfocused ultrasonic beam from the transducer array onto the workpiece in the first inspection zone;

d) storing a first echo signal from each transducer in the array generated by an echo received from the workpiece in the first inspection zone;

e) inverting the first echo signal from each transducer with respect to signal shape and time sequence and storing the inverted first echo signals;

f) rotating the workpiece in discrete steps to sequentially position n inspection zones adjacent to the array of ultrasonic transducers whereby the inspection zones are arranged in a generally circular configuration;.

g) repeating steps b)-f) for each of the n inspection zones on the workpiece;

h) transmitting the inverted first echo signals from the transducer array onto the workpiece in the same inspection zone from which the corresponding first echo signal was received;

i) storing a second echo signal from each transducer generated by an echo received from the workpiece;

j) inverting the second echo signal from each transducer with respect to signal shape and time sequence and storing the inverted second echo signal;

k) rotating the workpiece in discrete steps to sequentially position n inspection zones adjacent to the array of ultrasonic transducers whereby the inspection zones are arranged in a generally circular configuration; and, l) repeating steps h)-k) for each of the n inspection zones on the workpiece.

2. The method of claim 1 wherein the workpiece is a body of revolution and wherein the rotation of the workpiece comprises the step of rotating the workpiece about its axis of revolution whereby each inspection zone n comprises a sector of a circumferential area of the workpiece.

3. The method of claim 2 further comprising the step of relatively displacing the transducer array and the workpiece in a direction generally parallel to the axis of revolution after completion of step l)

4. The method of claim 3 wherein the displacement is carried out in discrete steps.

5. The method of claim 1 wherein the signals from the transducer are transmitted to the workpiece in a direction generally parallel to an axis of rotation of the workpiece such that each inspection zone n comprises a sector of an annulus.

6. The method of claim 5 comprising the additional step of displacing the workpiece relative to the transducer array in a direction generally perpendicular to the axis of rotation after completion of step l).

7. Apparatus for detecting internal defects in a workpiece comprising:

a) an array of ultrasonic transducers located so as to direct ultrasonic energy onto an inspection zone n of the workpiece, each transducer including receiver means to transmit echo signals therefrom;

b) rotation means to rotate the workpiece in discrete steps to sequentially position n inspection zones adjacent to the array of ultrasonic transducers whereby the inspection zones are arranged in a generally circular configuration;

c) first memory means connected to the transducer array to receive echo signals from the transducers, and to invert the echo signals with respect to signal shape and time sequence; and, d) second memory means connected to the first memory means so as to receive therefrom the inverted echo signals and store the inverted echo signals for each inspection zone on the workpiece and connected to the transducer such that the inverted echo signals [may be] are transmitted by the transducers onto the workpiece in the inspection zone n from which the corresponding echo signal was received.

8. The apparatus of claim 7 wherein the rotation means rotates the workpiece about an axis of symmetry.

9. The apparatus of claim 8 further comprising means to displace the workpiece and the transducer array relative to each other in a direction generally parallel to the axis of symmetry in discrete steps.

10. The apparatus of claim 7 wherein the rotation means rotates the workpiece about an axis, wherein the axis extends generally perpendicular to the transducer array.

11. The apparatus of claim 10 further comprising means to the move workpiece and the transducer array relative to each other in a direction generally perpendicular to the axis of rotation.

12. The apparatus of claim 7 wherein the second memory comprises a circulating buffer comprising memory locations equal in number to the number n of inspection zones.

13. The apparatus of claim 7 further comprising:

means to synchronize the rotation of the workpiece with transducer array such that inverted signals are transmitted onto the same inspection zone n from which the corresponding non-inverted echo signal was received.

14. The apparatus of claim 13 wherein the synchronization means comprises:

a) an encoder connected to the rotation means for rotating the workpiece for generating a first signal indicative of the rotational position of the workpiece;

b) a memory having means to input data and generate a second signal relating to the number of inspection zones n; and, c) comparator means to receive the first and second signals and connected to the transducer array.

\* \* \* \* \*